United States Patent
Cabal Mirabal et al.

(10) Patent No.: US 10,765,341 B2
(45) Date of Patent: Sep. 8, 2020

(54) FEET POSITIONING SYSTEM FOR MAGNETIC RESONANCE IMAGING STUDIES

(71) Applicant: Centro de Ingeniería Genética y Biotecnología, Playa, Havana (CU)

(72) Inventors: Carlos Alberto Cabal Mirabal, Havana (CU); Evelio Rafael González Dalmau, Havana (CU); Luis Manuel Flores Díaz, Havana (CU); Jorge Amador Berlanga Acosta, Havana (CU); Luis Saturnino Herrera Martinez, Havana (CU)

(73) Assignee: CENTRO DE INGENIERÍA GENÉTICA Y BIOTECNOLOGÍA, Playa, La Habana (CU)

( * ) Notice: Subject to any disclaimer, the term of this patent is extended or adjusted under 35 U.S.C. 154(b) by 36 days.

(21) Appl. No.: 14/900,244

(22) PCT Filed: Jun. 23, 2014

(86) PCT No.: PCT/CU2014/000003
§ 371 (c)(1),
(2) Date: Dec. 21, 2015

(87) PCT Pub. No.: WO2014/206379
PCT Pub. Date: Dec. 31, 2014

(65) Prior Publication Data
US 2016/0157750 A1    Jun. 9, 2016

(30) Foreign Application Priority Data
Jun. 24, 2013  (CU) .................................. 2013-0086

(51) Int. Cl.
*A61B 5/055* (2006.01)
*A61B 5/00* (2006.01)
(Continued)

(52) U.S. Cl.
CPC ............ *A61B 5/0555* (2013.01); *A61B 5/055* (2013.01); *A61B 5/6829* (2013.01); *A61B 90/39* (2016.02);
(Continued)

(58) Field of Classification Search
CPC ...... A61B 2090/363; A61B 2090/3954; A61B 5/055; A61B 5/0555; A61B 5/6829;
(Continued)

(56) References Cited

U.S. PATENT DOCUMENTS

| | | | |
|---|---|---|---|
| 5,361,764 A | 11/1994 | Reynolds et al. | |
| 2002/0022779 A1* | 2/2002 | Kose ..................... | A61B 5/055 600/422 |

(Continued)

OTHER PUBLICATIONS

Recht et al., "Selective Atrophy of the Abductor Digiti Quinti" An MRI Study, Musculoskeletal Imaging, American Roentgen Ray Society, Sep. 2007.

(Continued)

*Primary Examiner* — Amelie R Davis
(74) *Attorney, Agent, or Firm* — Hoffmann & Baron, LLP (57) ABSTRACT

The present invention is related to a system and method to ensure the reproducibility of the position of the feet and lower parts of the legs during Magnetic Resonance Imaging (MRI) studies, and to obtain robust quantitative information through the time. The system includes a device that is inserted into the radiofrequency coils of any MRI equipment. The device includes a foot support section, a leg support section and a base adapted to allow that the above-mentioned sections be fixed in it. With this device and method, and through external and internal markers, quantitative studies of the evolution of pathophysiological phenomena that affect the anatomy and physiology of the feet and lower parts of the legs are performed.

7 Claims, 6 Drawing Sheets

(51) Int. Cl.
*A61B 90/00* (2016.01)
*A61N 5/10* (2006.01)
*A61G 13/12* (2006.01)

(52) U.S. Cl.
CPC . *A61B 2090/363* (2016.02); *A61B 2090/3954* (2016.02); *A61G 13/125* (2013.01); *A61G 13/1245* (2013.01); *A61N 2005/1055* (2013.01); *A61N 2005/1097* (2013.01)

(58) Field of Classification Search
CPC .. A61B 90/39; A61G 13/1245; A61G 13/125; A61N 2005/1055; A61N 2005/1097
See application file for complete search history.

(56) References Cited

U.S. PATENT DOCUMENTS

| | | | |
|---|---|---|---|
| 2004/0199072 | A1 | 10/2004 | Sprouse et al. |
| 2005/0080333 | A1 | 4/2005 | Piron et al. |
| 2007/0053502 | A1 | 3/2007 | Zelnik et al. |
| 2007/0250047 | A1* | 10/2007 | Harter ............ A61B 5/0555 606/1 |
| 2008/0161815 | A1* | 7/2008 | Schoenefeld ...... A61B 17/154 606/87 |
| 2009/0048505 | A1* | 2/2009 | Kuth ............... A61B 5/0555 600/410 |
| 2009/0308400 | A1 | 12/2009 | Wilson et al. |
| 2010/0192961 | A1* | 8/2010 | Amiot ............... A61G 13/12 128/882 |
| 2012/0053490 | A1* | 3/2012 | Smith .............. A61B 5/0082 600/592 |
| 2012/0143628 | A1 | 6/2012 | Miller et al. |
| 2013/0053677 | A1 | 2/2013 | Schoenfeld |
| 2013/0204119 | A1* | 8/2013 | Coelho Do Sameiro Espregue Mendes ...................... A61B 5/103 600/411 |

OTHER PUBLICATIONS

Kapoor et al., "Magnetic Resonance Imaging for Diagnosing Foot Osteomyelitis," Arch Intern Med., vol. 167, p. 125-132, Jan. 2007.
Sormaala et al., "Comparison of 1.5T and 3T MRI scanners in evaluation of acute bone stress in the foot," BMC Musculoskeletal Disorders, 2011.
Sung et al., "Diagnosis of Plantar Plate Injury by Magnetic Resonance Imaging with Reference to Intraoperative Findings," The Journal of Foot & Ankle Surgery, vol. 51, p. 570-574, 2012.
Greenman et al., "Foot Small Muscle Atrophy Is Present Before the Detection of Clinical Neuropathy," Diabetes Care, vol. 28, No. 6, p. 1425-1430, Jun. 2005.
Johnson et al., "Diagnostic Utility of T1-Weighted MRI Characteristics in Evaluation of Osteomyelitis of the Foot," Musculoskeletal Imaging, American Roentgen Ray Society, Jan. 2009.
Andreassen et al., "Accelerated atrophy of lower leg and foot muscles—a follow-up study of long-term diabetic polyneuropathy using magnetic resonance imaging (MRI)," Diabetologia vol. 52, p. 1182-1191, Mar. 2009.
Kudo et al., "Round cell liposarcoma arising in the left foot: MRI and PET findings," Japan Radiological Society, vol. 30, p. 852-857, 2012.
Sangeux et al., "Quantification of the 3D relative movement of external marker sets vs. bones based on magnetic resonance imaging," ScienceDirect, Clinical Biomechanics 21, p. 984-991, 2006.
Suzuki et al., "1H- and 31P-magnetic resonance spectroscopy and imaging as a new diagnostic tool to evaluate neuropathic foot ulcers in Type II diabetic patients," Diabetologia vol. 43, p. 165-172, 2000.
Lipsky et al., "Diagnosis and Treatment of Diabetic Foot Infections," Guideline for Diabetic Foot Infections, Clinical Infectious Diseases, vol. 39, p. 885-910, 2004.
Edelman et al., "Prognostic Value of the Clinical Examination of the Diabetic Foot Ulcer," J Gen Intern Med, vol. 12, p. 537-543, 1997.
Robinson et al., "Surgical aspects of the diabetic foot," Bone and Joint Surgery, vol. 91-B, No. 1, p. 1-7, Jan. 2009.
Poll et al., "Routine MRI findings of the asymptomatic foot in diabetic patients with unilateral Charcot foot," BioMed Central, Diabetology & Metabolic Syndrome, 2010.
Thomas et al., "Osteomyelitis and Lower Extremity Amputations in the Diabetic Population," The Journal of Diabetic Foot Complications, vol. 2, Issue 1, No. 4, p. 18-27, 2010.
Moholkar et al., "Imaging benign soft tissue lesions of the foot," Applied Radiology, p. 10-21, 2009.
Vartanians et al., "Is there a role for imaging in the management of patients with diabetic foot?," Skeletal Radial., vol. 38, p. 633-636, 2009.
Moreno Casado et al., "Diabetic foot. Findings on MR Imaging," Revista Internacional de Ciencias Podologicas, vol. 4, No. 1, p. 45-53, 2010.
Tan et al., "MRI of the diabetic foot: differentiation of infection from neuropathic change," The British Journal of Radiology, vol. 80, p. 939-948, 2007.
Collins et al., "T1-Weighted MRI Characteristics of Pedal Osteomyelitis," Musculoskeletal Imaging—Clinical Observations, p. 386-393, 2005.
Craig et al., "Osteomyelitis of the Diabetic Foot: MR Imaging-Pathologic Correlation," Radiology, vol. 203, p. 849-855, 1997.
Mundwiler et al., "The utility of MRI in predicting radiographic erosions in the metatarsophalangeal joints of the rheumatoid foot: a prospective longitudinal cohort study," Arthritis Research & Therapy, p. 1-10, 2009.
Kavanagh et al., "MRI of Trauma to the Foot and Ankle," Semin Musculoskelet Radiol, p. 308-327, 2006.
Freund et al, "The foot in multistage ultra-marathon runners: experience in a cohort study of 22 participants of the Trans Europe Footrace Project with mobile MRI," BMJ Open, p. 1-8, 2012.

\* cited by examiner

FEET POSITIONING SYSTEM FOR MAGNETIC RESONANCE IMAGING STUDIES

This application is the U.S. National Phase of, and Applicant claims priority from, International Patent Application Number PCT/CU2014/000003 filed Jun. 23, 2014, which claims priority from CU2013-0086 filed Jun. 24, 2013, each of which is incorporated herein by reference.

TECHNICAL FIELD

The present invention is related to the fields of human medicine, the pharmaceutical industry and biomedical research. In particular, it is applicable to radiology, sports medicine, angiology, endocrinology, orthopedics, rheumatology and traumatology. It enables quantitative Magnetic Resonance Imaging (MRI) studies of the feet and the lower parts of the legs.

BACKGROUND OF THE INVENTION

A large set of inflammatory, degenerative, traumatic, infectious, autoimmune, orthopedic, vascular and neurological diseases are affecting the anatomy and physiology of the feet and the lower parts of the legs. The causes of these conditions and their treatments are very different. The foot diseases disturb in varying degrees the body. There are growing numbers of people during their professional activities (sportsmen, artists, military) that subject the lower extremities, including the feet, to high stress. On the other hand, there are multiple conditions and of high incidence affecting the lower limbs, such as diabetic foot ulcers (DFU), rheumatoid arthritis, deformities, inflammations and infections, circulatory, traumatic, and neuropathic conditions, among others. Methods of diagnosis of foot diseases and the lower parts of the legs are still insufficient.

The foot studies with images is a current scientific and clinical problem, with a growing number of works devoted to the subject [Suzuki E. *Diabetologia* (2000), 43: 165-172; Greenman R L., *Diabetes Care* (2005), 28: 6:1425-30; E. G Kavanagh, A. C Zoga, *Seminars in Musculoskeletal Radiol* (2006), 10: 4 308-27; Kapoor A, *Arch Intern Med.* (2007), 167:125-132; Johnson P. W, *AJR* (2009), 192: 96-100; Andreassen C. S., *Diabetologia* (2009), 52: 1182-1191; Moreno Casado M. J, *Revista Intern. Ciencias Podológicas* (2010), 4: 45-53; Poll L. W, *Diabetology & Metabolic Syndrome* (2010), 2: 2-5 (http://www.dmsjournal.com/content/2/1/25); Ramoutar C T, *The J of Diabetic Foot Complications* (2010), 2: 18-27; M. J. Sormaala, et al., *Musculoskeletal disorders* (2011), 12: 1-6; H. Kudo, et al. *Jpn. J. Radiol* (2012), 30: 852-857; W L. Sung, et al., *The J. of Foot and Ankle Surgery* (2012), 50: 570-574; Freud W., *BMJ Open* (2012), 2: 1-8]. In those cited works, the methods used are X-ray, Ultrasound, Computed Tomography, different modalities of nuclear medicine and MRI. Recent publications make comparative assessments of the aforementioned technologies to study the many foot conditions [B A Lipsky, et al. *Clinical Infectious Diseases* (2004), 39:885-910; Moholkar S, *Appl. Radiology*, www.appliedradiology.com, October (2009); Vartanians V. M, et al. *Skeletal Radiol* (2009), 38:633-636; Thomas-Ramoutar C, *The J of Diabetic Foot Complications* (2010), 2:18-27]. All imaging modalities are complementary. However, more and more articles give preference to the MRI for its non-invasiveness, sensitivity for the study of soft parts, its high spatial resolution and unmatched contrast, while providing anatomical and functional information [M. L. Mundwiler, et al. *Arthritis Research and Therapy* (2009), 11: 3, 1-10; Vartanians V. M, et al., *Skeletal Radiol* (2009), 38: 633-636; M. J. Sormaala, et al., *Musculoskeletal disorders*, (2011), 12: 1-6; H. Kudo, et al. *Jpn. J. Radiol* (2012), 30: 852-857; W L. Sung, et al., *The J. of Foot and Ankle Surgery* (2012), 50: 570-574].

However, in 2007, a published research describes a study of 602 patients with selective fat atrophy; they concluded that MRI diagnosis is uncertain [M. P. Recht, et al. *AJR* (2007), 189: W123-W127]. The cause of this conclusion is that patients were not studied under the same positioning conditions. The vast majority of MRI reports perform a qualitative assessment of the status of the foot, without giving continuity to the evolution (longitudinal studies), and those that do it, do not show guarantees of making it under equal conditions. Therefore, their conclusions are often cautious or are inconsistent with other work. For example, Edelman made a study of the clinical course of 63 DFU patients during six months [Edelman, D., *J. Gen Intern Med* (1997), 12: 537-543], concluding that the provision of MRI information is not determinant in differentiating osteomyelitis from other infectious conditions failing to predict the cure. In contrast, in another study [Kapoor A, *Arch Intern Med.* (2007), 167: 125-132], from a meta-analysis, data from different authors are discussed, comparing the sensitivity and specificity of MRI with conventional radiography and methods of technetium 99. At the same, it was demonstrated that MRI have higher specificity and sensitivity, for studies of osteomyelitis, than the other methods. Affirmations from the work published by Edelman in 1997 are inconsistent with works by other authors [Craig J C, *Radiol.* (1997), 203: 849-855; B A Lipsky, et al. *Infections Clinical Infectious Diseases* (2004), 39: 885-910; Collins M. S, *AJR* (2005), 185: 386-393; Kapoor A, *Arch Intern Med.* (2007), 167: 125-132; Tan, P L Teh J.; *The British J. of Radiol* (2007), 80: 939-948; Robinson A. H. N, *J Bone Joint Surg* [Br] (2009), 91-B: 1-7; Johnson P. W, *AJR* (2009), 192: 96-100]. In particular, in the work published by Craig the results of 15 MRI tests are correlated with the histopathology of 57 samples, proving prospectively that the diagnostic sensitivity was 90%, and the specificity was 71% [Craig J C, *Radiol* (1997), 203: 849-855]. Other authors declare different values for sensitivity and specificity, always above 50%, depending on the entities and comparison methods [Collins M. S, *AJR* (2005), 185: 386-393; Johnson P. W, *AJR* (2009), 192: 96-100; Thomas-Ramoutar C, *The J of Diabetic Foot Complications* (2010), 2: 18-27]. On the other hand, Freud W et al [Freud W., *BMJ Open* (2012), 2, 1-8] made a MRI study of the feet of 22 athletes, along a marathon race, at the beginning and during different stages of the race, to assess the effects caused by stress. In it, the size of the Achilles tendon and its distance to different lesions were measured. However, although the presence of edema is reported, the volume and the variation thereof were not measured. The reserved conclusions of this work do not have a rigorous quantitative foundation. The conformity between the different studies (of the feet and legs) together remains an unsolved problem. Quantitative and evolutionary evaluations of the different diseases that affect the feet are insufficient.

These discrepancies in the results, and the absence of reliable evolutionary quantitative studies, have some main reasons: the feet are structures of high biological variability between individuals, the feet have high mobility and their anatomical-functional characteristics are complex (they have 26 bones, 33 joints, 126 muscles and more than 100 tendons, vascular and nerve terminals with high mechanical load).

The patent application U.S. 2013/0053677 claims a device, a scanner, for studying foot lesions. In said patent document the plantar surface of the foot is scanned, and a three-dimensional reconstruction of the outer surface of the foot (foot skin) is done with software. This device and method do not allow the display, less the measurement of internal bone structures, muscles, ligaments, joints and their alterations. It applies only to some of the conditions of dermal nature in the plantar surface of feet. It does not solve the visualization, quantification and monitoring of the vast majority of diseases of the feet, as the DFU (appearing in any area of the feet, at different depths), rheumatoid arthritis, deformities, inflammations and infections, neuropathic and circulatory disorders, among others. This device is not connected to MRI studies. Moreover, only one foot is evaluated, which does not allow the comparison between them in the same conditions. Meanwhile, the patent application WO 2012/143628 A1 discloses a device and an orthopedic mechanic method for evaluating only partial damages of the anterior ligament of the knee.

The quantification of anatomical and physiological processes on the surface and inside of the foot, to provide new qualitative and quantitative information, and evolutionary information, virtually for all diseases of the lower extremities is not solved with these inventions.

In MRI foot studies the main problem is to obtain evolutionary and quantitative information of the several feet diseases, (including inflammatory processes that alter the sizes and relative locations of the anatomical structures) requiring that a fixed and reproducible position be achieved, along the different tests. To have quantitative information of existing pathophysiological processes in the feet and lower parts of the legs and their evolution, either spontaneously or as a result of treatments remains as an unsolved problem.

DESCRIPTION OF THE INVENTION

The present invention solves the problem mentioned above, by providing a system for controlling the orientation of the feet with respect to MRI equipment, during the scan process, comprising a positioning device of the foot, wherein said device comprises: (a) a foot support section which includes a foot surface stand (for placing at least one foot of the subject in a fixed position relative to the device), comprising at least two elements that are imaging markers which are visible when the MRI are recorded; a heel arch adapted to be positioned behind the heel and sliding relative to said surface for the foot; and gadget to fix the patient feet on such support surface during the scan; (b) a leg support section comprising: a leg support for positioning at least one leg of said person in a fixed position relative to the device; gadget to fix the patient legs on such support surface during the scan; and (c) a device base, adapted to hold in it the foot support surface and the leg support section.

The system and device of the invention ensure the fixed and reproducible position of the feet, and the lower parts of the legs, which is an essential and exceptionally complex process, for serial quantitative studies. This solution reaches even cases of patients with inflammatory processes and other disorders for which the assessment of the dimensions and the relative positions of the anatomical parts is difficult.

With the system of the invention quantitative measurements of area, volume, texture of the anatomical structures of the feet and the lower parts of the legs can be performed, valuable quantitative information to assess the effectiveness of different treatment schemes for diseases that affect the feet and lower parts of the legs.

In an embodiment of the invention, the support section of the foot, movably respect the base, can be placed in a number of determined positions with respect to the base and indicated on a scale.

In an embodiment of the invention, in the system being object of the same, the device for positioning the foot is adapted to engage the equipment for MRI in a reproducible position with respect to the axis of the main static magnetic field of MRI equipment.

In the system of the invention, the foot support surface comprises at least two image markers which are visible when MRI is recorded. This system allow that a foot may be the control of the other if it is necessary, and ensure reproducibility and error evaluation of the position of the feet, ankles and lower parts of the legs, through external markers and internal biomarkers for serial quantitative studies with MRI. In a particular embodiment, in the device for positioning the foot, the image marker elements are positioned in parallel to said foot support surface defining a MRI plane. The other planes are taking perpendicularly to the plane defined by the MRI markers. In a materialization of the invention, the device for foot positioning is made of substantially invisible material under MRI visualization. In a particular case, the material is polyvinyl chloride (PVC).

In an invention embodiment, said device comprises two support surfaces for the foot, two arcs for the heels, and two leg support surfaces, all positioned next to each other on the base of the device, in the way that the device allows the simultaneous examination of both feet and lower parts of the legs of the individual during MRI scan.

In a materialization of the invention, in the system object of the invention, the device for positioning the foot is adapted to be inserted into a rigid radiofrequency (RF) coil of a MRI system. With the system and device of the invention, immobilization and reproducibility of the position of feet and the lower parts of the legs is guaranteed. This device is designed and constructed such that it is mechanically and electromagnetically compatible with MRI equipment, and can be placed in the RF coil. In a particular case, the RF coil where the foot positioning device is inserted is a head coil.

The foot positioning device is made of non-magnetic material, and its electromagnetic properties, in particular electric and magnetic permeabilities do not alter the uniformity and intensity of the RF field, and the quality factor (Q) of the RF reception coil. The material for the construction of the device must be rigid, lightweight, not rugged, and resistant to frequent cleanings and disinfections.

Figure 1A:
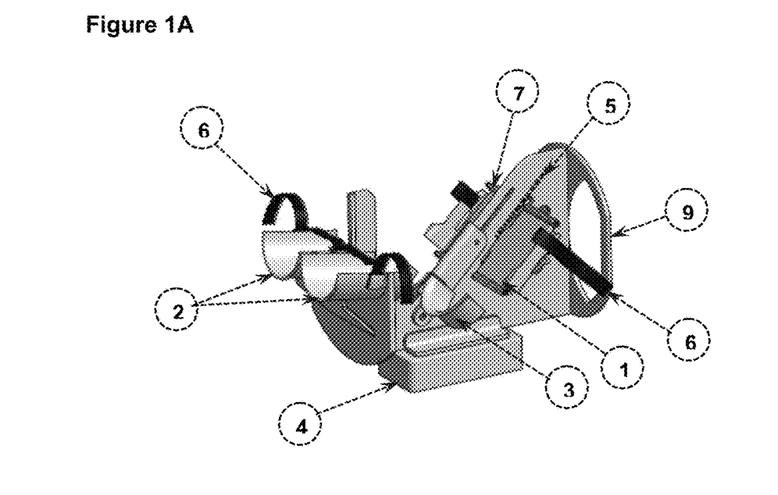
Figure 1B:
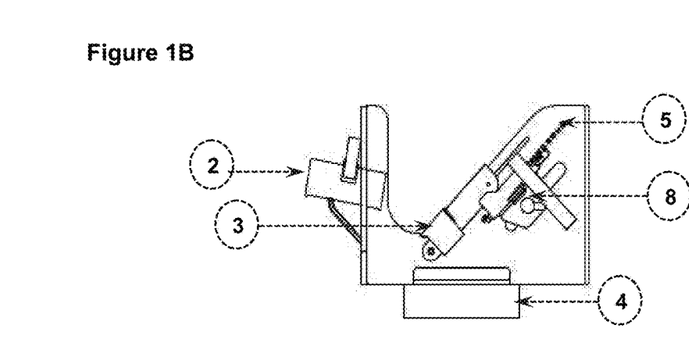

For a better understanding of the invention, FIG. 1 shows a diagram (isometric, side and front views) of the essential portions of one of the devices that are part of the invention, but the diagram does not constitute a limitation to it. Said device comprises: (a) a foot support section which includes a foot support surface(1), for positioning at least one foot of said individual in a fixed position relative to the device, wherein said support surface comprises at least two image marker items (7) that are visible when the MRI are recorded; an arc for the heel (3) adapted to be positioned behind the heel of the individual and sliding relative to said surface for the foot; and means (6) to set the foot of the individual on such support surface during the scan; (b) a leg support section, comprising: a leg support (2), for placing at least one leg of said person in a fixed position relative to the device; and means (6) to fix one leg of the individual to said leg support (2) during the scan; and (c) a device base (4) adapted to allow that the foot support surface and the leg support section being fixed on it.

Figure 1C:
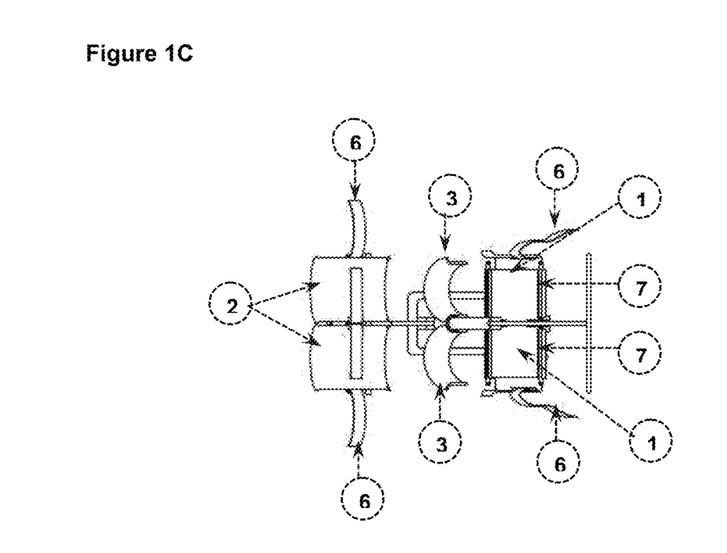

The device shown in FIG. 1 has two foot support surfaces (1) suitably located in the front part, so as to secure the position of both feet which form a proper angle with the supports for proper placement of the legs (2), and let both legs to be in the same plane, the same orientation, and in the best homogeneity zone of the RF field of the coil. In addition, the device has arches for the heel (3), to ensure the location of the calcaneus of both feet. Optionally, both the supports (2) and the heel arches (3) may be coated with a soft material. In the same figure is shown the base of the device (4) which permits to fix it to the RF coil, or the patient bed, as appropriate, according to the MRI equipment model. The support surfaces of the foot (1) slide, and their position is marked according to the scale (5). Also, in FIG. 1A and 10 bands (6) are shown for securing the feet and legs of the individual to the respective supports, during scan. FIG. 2 details the leg supports (2), the surfaces of the foot supports (1), and the arches for the heel (3).

Figure 2A:
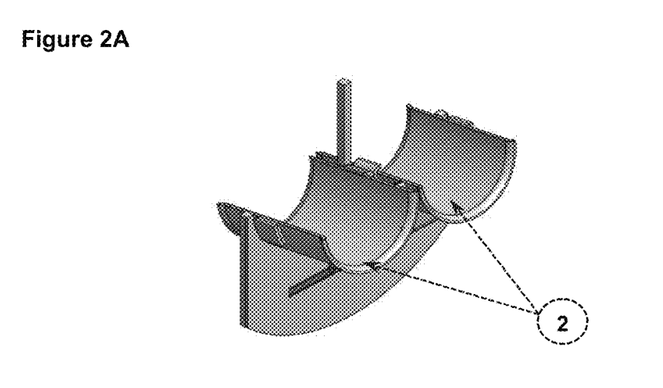
Figure 2B:
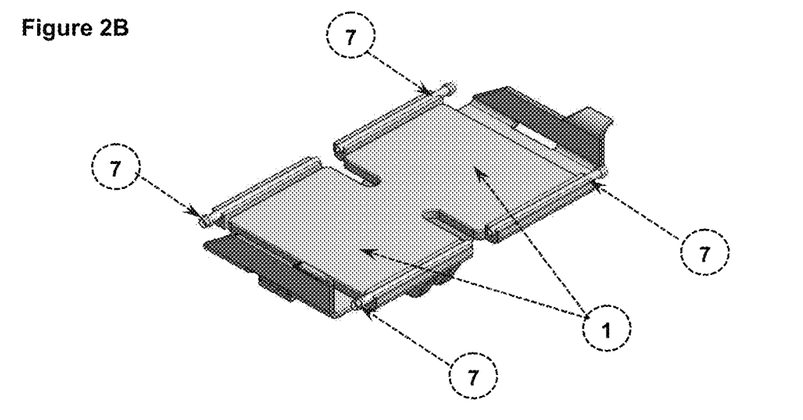
Figure 2C:
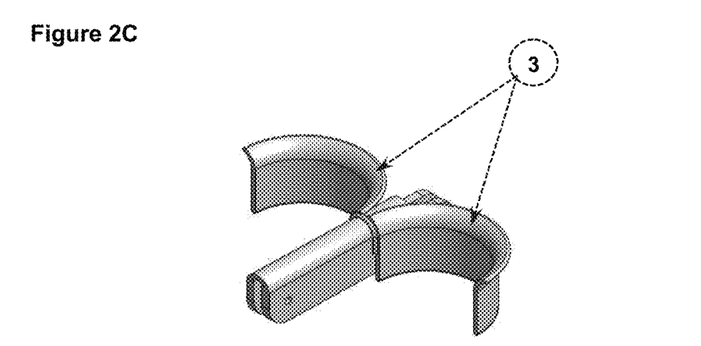
Figure 3A:
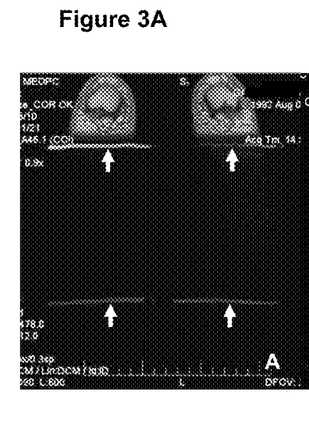
Figure 3B:
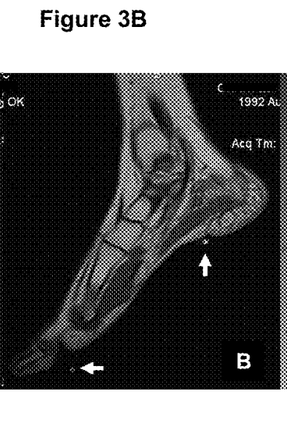
Figure 3C:
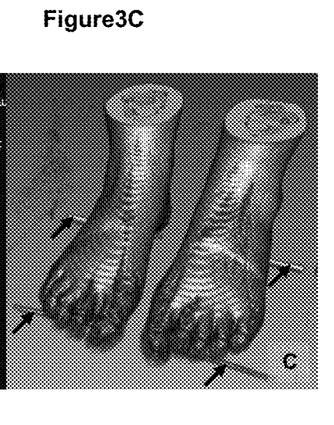

A cardinal element of the device is shown in FIGS. 1 and 2 with number 7. There are four external markers, which are parallel and at the same level of the supporting surface 1. These external markers consist in conveniently sealed tubes filled with an electrolytic solution, whose magnetic relaxation time Spin-Reticle (T1) and Spin-Spin (T2) are similar to the T1 and T2 of the foot tissues. These two line segments determine a single geometric plane. FIG. 3 shows images of coronal sections (FIG. 3A), sagittal (FIG. 3B), and the three-dimensional reconstruction of the feet (FIG. 3C), where the external markers are indicated.

The device of FIG. 1 also comprises a pin (8) for adjusting the positions of the two supports 1 in unison, as by the dimensions of the feet. Pin 8 releases and fixes at the same time both support surfaces 1. Conveniently, the device has a gripping groove (9), which allows the operator of the MRI equipment to hold the device with one hand, for transfer and placement, without making contact with its others parts. To check for any changes in the electromagnetic characteristics of the RF coil, when the device is used for the first time, MRI are recorded with a standard object (phamton) before placing it, and once it is placed. On the MRI of the phantom are measured the RF field homogeneity, the signal-to-noise and contrast-to-noise ratios in accordance with NEMA international standards ["MS 6-2008; MS 8-2008: "MS 9-2008, NEMA].

Figure 4:
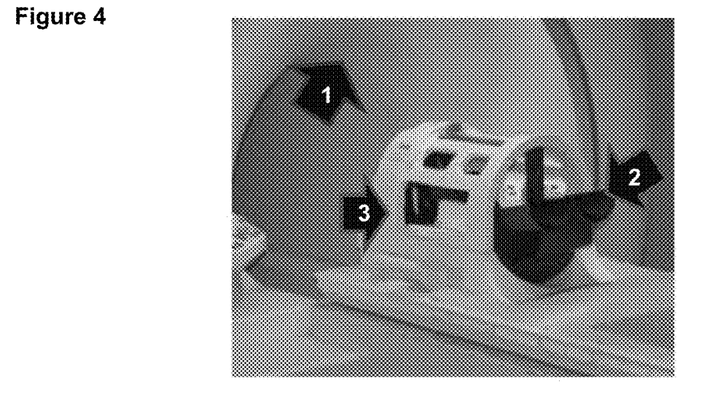
FIG. 4. Example of device positioning in a MRI head RF coil. Arrow 1 indicates the MRI magnetic system, arrow 2 shows the positioning and cramping device, and arrow 3 indicates the complete RF coil.

Another object of the present invention is a method for controlling the orientation of the foot of an individual, with respect to a MRI system during the scan of the images, comprising: (a) to locate a foot positioning device in a fixed and reproducible position in the RF coil of the MRI system (see FIG. 4); (b) to situate the foot of the individual in such a device for foot positioning, in a reproducible and fixed position in relation to the imaging marker elements, which are allocated within the device in a way that determine a plane that is a reference for the rest of the MRI planes of the feet of the individual; (c) to record the MRI in order to check the correct positioning of the foot; (d) to amend, if necessary, the foot position of the individual in relation to the markers and the device in the MRI system; and (e) to record the MRI.

In an embodiment of the invention, in said method, additionally internal biomarkers are used to check the positioning of the foot, and the error along different consecutive MRI records. For the invention purposes it is defined as an internal biomarker an anatomical structure, of area and volume measurable in a reproducible manner, remote from the area affected by the disease under study.

In an invention embodiment in the method for controlling the orientation of the foot with respect to a MRI system, the device for the foot positioning is a device comprising: (a) a foot support section, including a foot support surface for positioning at least one foot of said subject in a fixed position in relation to the device; a heel arch adapted to be positioned behind the heel of the individual and sliding in relation to said surface for the foot; and means to fix the foot of the individual on such support surface during the scan; (b) a support section for the foot, comprising: a leg support for positioning at least one leg of said person in a fixed position relative to the device; and means for securing a leg of the individual to said leg support during the scan; and (c) a device base, adapted to hold in it the foot support surface and the leg support section. In a particular materialization of the method of the present invention, the device for foot positioning is shown in FIG. 1.

BRIEF DESCRIPTION OF THE FIGURES

FIG. 1. Schematic representation of a device for positioning and fixation of the feet during MRI scanning. A. Isometric view, B. Lateral view, C. Top view of the device. In the views are shown the main parts of the device: 1. Foot support surface, 2. Leg support 3. Arch for the heel, 4. Device base, 5. Scale, 6. Means to fix feet and lower part of the legs, 7. Image markers (external), 8. Pin, and 9. Grip groove.

FIG. 2. Details of leg supports in the device (2 in FIG. 2A), Foot support surface (1 in FIG. 2B), and arches for the heel (3 in FIG. 2C).

FIG. 3. MRI of healthy foot. Arrows indicate the position of the external markers in coronal section (A), sagittal section (B) and in a three-dimensional image reconstruction of the feet (C).

FIG. 6. Orientation of the MRI sections for foot studies. The coronal section (A) is taken parallel to the plane determined by the external markers on the surface where the foot sole is placed. The sagittal (B) and the axial (C) sections are orthogonal to the coronal section.

FIG. 7. Sagittal MRI section taken at two different times (A and B), to the same healthy volunteer.

FIG. 8. MRI axial section of a DFU patient, taken before and during treatment with epidermal growth factor (EGF). A. Before treatment (week 0); B. at week 9; C. at week 14; and D. at week 28 after the beginning of the treatment.

FIG. 9. Variations of the area (A) and volume (B) of the DFU of a patient at weeks 0, 9, 14 and 28 of the treatment with EGF. The area and volume were measured starting from MRI.

FIG. 10. Three-dimensional reconstruction of the edema volume, at three different times, starting from MRI of a DFU patient treated with EGF. The darkest area is the edema. A. Before treatment, week 0; B. at week 6; and C. at week 10 of the treatment. The thick black and white arrow indicates the DFU. The white arrow indicates the area affected by the edema.

FIG. 13. MRI of the foot of a DFU patient (axial section), obtained with the system and method of the invention, during the EGF treatment. A. Before treatment; B. at week 6 of treatment; and C. at week 7 of treatment. The arrow in A and B indicates the lesion, and in C shows a hyperintense area, related to the appearance of new epithelial tissue as a consequence of treatment.

FIG. 14. Temporal evolution of the calcaneus infection in a patient, studied through MRI obtained with the system and method of the invention. A. week zero; B. week 6; and C. week 8 of the study. The arrow indicates the site of infection.

EXAMPLES

The following examples are shown for illustrative purposes, and should not be considered as limiting the invention.

Example 1

Positioning of the Individual

The first step to ensure reproducibility of quantitative measurements for the scan of MRI was to correctly position both feet and legs of the individual in the device shown in FIG. 1, coupled to the RF coil of the MRI equipment. The individual lays face up (supine) in the equipment bed with his legs towards the entrance of the magnetic system, as illustrated in FIG. 5.

The feet and the lower parts of the legs were placed and fixed, to obtain simultaneously MRI (e.g., coronal and axial sections) and Magnetic Resonance Spectra (MRS) of both feet, without changing the position. This allowed us to compare, on an equal condition, both limbs along the studies, and so that a lower member serves as reference to the other one.

Each foot carefully rested on the support surfaces 1 and heels were leaned on arches 3. At unison, the lower parts of the legs were supported on supports 2, which were conveniently fitted with pins 8, according to the dimensions of the feet. The positions of the support surfaces 1 and the heel arches 3 on the scale attached to the device (denoted by 5) were recorded.

Figure 5:
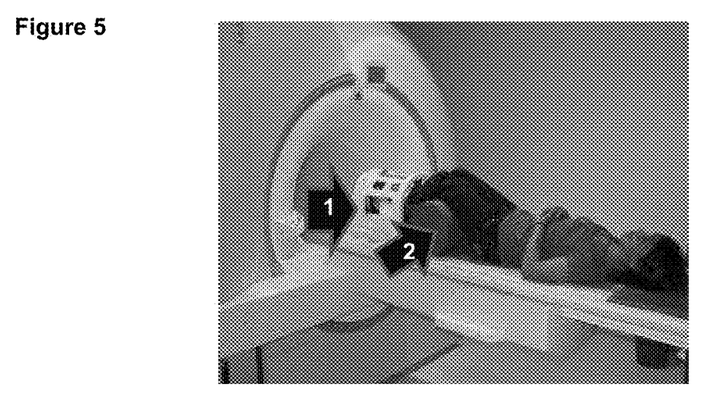
FIG. 5. Position of the individual examined with the feet in the positioning device, inside the head coil, in the MRI equipment indicated with arrow 1. Arrow 2 indicates a pillow standing on the back of the knees of the individual.

People examined bent the legs slightly, as shown in FIG. 5, to feel comfortable. Below the knee backs was placed a cushion, so they could rest their legs on it. Then the means for securing the feet and lower parts of the legs were adjusted (indicated as 6) to prevent that involuntary movement of the examined person change the position of the feet or lower parts of the legs.

Example 2

Checking and/or Correction of the Position of the Feet

Once positioned the feet of the individual, he was placed at the isocenter of the magnet system, and proceeded to record the planning MRI in three sections: coronal, sagittal and axial. The MRI showed the external markers 7. The correct position of the feet was checked, so that the MRI of soles appeared fully supported on the support surfaces 1, determined by the pairs of external markers 7 for each foot. In case the positioning was not correct, it was corrected as in Example 1. If the positioning was correct, the final planning of study sections proceeded.

Example 3

Planning and Orientation of the Sections

The first section to be recorded was oriented parallel to the plane determined by the external markers, although it could be any plane, according to a preset angle in reference to the one determined by such markers. Other necessary sections were determined in connection with this first one, according to the study to be performed.

Figure 6A:
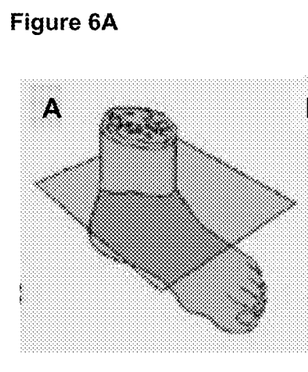
Figure 6B:
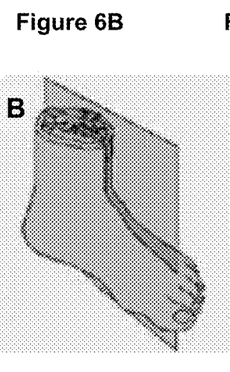
Figure 6C:
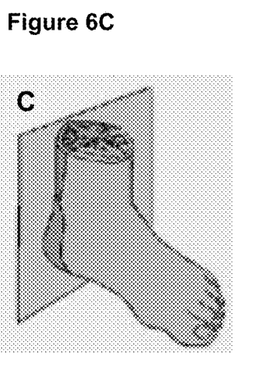

In FIG. 6 is shown the orientation of the sections planned and applied in Examples 4 to 10. The coronal section (FIG. 6A) is taken parallel to the plane determined by the external markers, and the other two sections (sagittal, FIG. 6B and axial, FIG. 6C) are orthogonal to the initial coronal section.

Example 4

Determination of Internal Markers: Position of Anatomical Structures

In addition to external markers (denoted as 7), there were established internal controls that allowed determining the position, its reproducibility and evaluation of error in the serial MRI studies. This was essential, especially for those patients with inflammatory processes, since in these cases the determination of the sizes and relative positions of the anatomical parts and their evolution, either naturally or due to treatment regimens, is difficult.

Figure 7A:
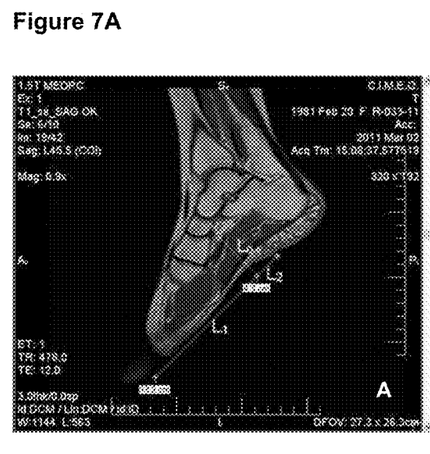
Figure 7B:
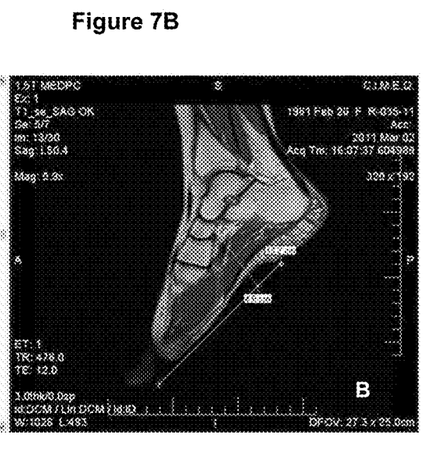
Figure 8A:
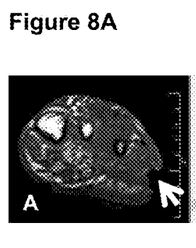
Figure 8B:
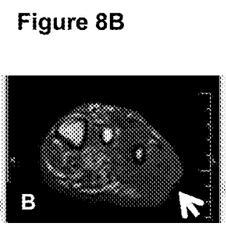
Figure 8C:
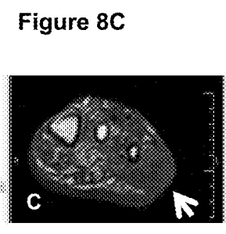
Figure 8D:
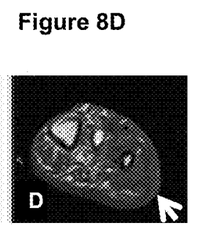

As an internal marker it was defined an internal anatomical structure of the foot, which was chosen in the way that it was not affected or it was far from the pathological processes affecting the foot, in particular the inflammatory ones. In this case it was taken as an internal marker the perpendicular distance $L_o$ from the center of the tolocalcaneum interosseum ligament to the segment joining the two external markers (see FIG. 7). The $L_0$ distance and this perpendicular segment connecting the two external markers determine exactly one plane. Both distances were measured from sagittal sections of MRI (FIG. 7). In this figure, as an example, two sagittal planes are shown taken to the same volunteer, in two separate studies, at different time moments are shown. It measures distances taken on the image between the two external markers are indicated. In this example, $L_0=13.2$ cm in both FIGS. 7A and 7B). The $L_1$ segment is also shown, which is perpendicular to the line $L_0$, and runs from the intersection point of $L_0$ with the line that connects the external markers to the furthest external marker. Furthermore, $L_2$ is the distance in the image from the intersection of $L_0$ to the line that connects the external markers to the posterior external marker position, as shown in FIGS. 7A and 7B. The two distances $L_1>L_2$, were selected of different sizes, to provide two different sensitivities facing a possible relative error. A change of orientation of the foot position will imply a change of distances $L_1$ and $L_2$. Moreover, if the deviations of $L_1$ and $L_2$ are small and they are known then changes above these values are attributable only to morphological variations of the foot.

In Table 1 the values of $L_1$ and $L_2$ measured on images from 10 healthy volunteers are shown, recorded at two different times, in which the feet were always placed in identical positions. Surprisingly, as shown in Table 1, the mean changes $\Delta L_1$ and $\Delta L_2$ (variation between two successive positions in two different studies), are less than 1.0 mm (The maximum variation was 6.7%), which evidences how robust the device and the procedure are.

TABLE 1

Criteria of the feet correct positioning. Measurements $L_1$ and $L_2$ in the sagittal MRI sections of 10 healthy volunteers studied in two separate occasions.

| | | | 1 | 2 | 3 | 4 | 5 | 6 | 7 | 8 | 9 | 10 |
|---|---|---|---|---|---|---|---|---|---|---|---|---|
| Volunteer No | | | | | | | | | | | | |
| Length (mm) | Study 1 ($S_1$) | $L_1$ | 71 | 54 | 58 | 64 | 65 | 69 | 60 | 44 | 68 | 55 |
| | | $L_2$ | 13 | 5 | 7 | 7 | 8 | 20 | 16 | 31 | 13.5 | 16 |
| | Study 2 ($S_2$) | $L_1$ | 70 | 54 | 57 | 62 | 65 | 69 | 58 | 42 | 66 | 54 |
| | | $L_2$ | 13 | 5 | 7 | 7 | 8 | 19 | 15 | 31 | 14 | 17 |
| | Δ between studies ($\Delta L_x = L_{xS1} - L_{xS2}$) x = 1 ó 2 | $\Delta L_1$ | 1 | 0 | 1 | 2 | 0 | 0 | 2 | 3 | 2 | 1 |
| | | $\Delta L_2$ | 0 | 0 | 0 | 0 | 0 | 1 | 1 | 0 | −1 | −1 |
| | % Variation ($\Delta L_x/L_{xS2}*100$) | $\Delta L_1$ | 1.4 | 0 | 1.8 | 3.2 | 0 | 0 | 3.4 | 4.5 | 3.0 | 1.9 |
| | | $\Delta L_2$ | 0 | 0 | 0 | 0 | 0 | 5.3 | 6.7 | 0 | 3.6 | 5.9 |

ΔL1 and ΔL2 are variations of $L_1$ and $L_2$ from a single healthy volunteer from one study to another, at different times.

Example 5

Determining Internal Markers: Anatomical Structures Area

Besides the external markers (indicated as 7), and the first internal marker described in Example 4, a second internal marker was defined as the area of a predetermined anatomical structure, according to MRI assessments that were required to perform.

In this example, to illustrate, this second internal marker was defined as the areas of multiple calcaneus coronal sections. Five different coronal sections were chosen. The record of multiple coronal sections ensures several evaluations from different areas, located at dissimilar distances of possible inflammatory processes or changes in other regions of the foot and/or lower parts of the leg.

The ratio of the measured areas in different studies, on images of different structures, was an undeniable internal control of foot positioning and orientation of the sections. This internal marker is totally conclusive, complements and is consistent with the results presented and related to the first internal marker (Example 4).

In serial studies performed under the conditions described, variations in the size of different parts of the foot were below 4.5%. Any variation greater than this value is attributable solely to the evolution of pathophysiological processes of the feet. In Table 2, the coefficient of variation of the calcaneus area is shown, measured in five coronal sections, at two different times, in 10 volunteers.

TABLE 2

Demonstration of the reproducibility of the feet position calculated from the calcaneus area as a second internal marker.

| | | Different sections of the calcaneus | | | | |
|---|---|---|---|---|---|---|
| | | I | II | III | IV | V |
| Coefficient of variation % (10 volunteers) | 1 | 0.86 | 1.48 | 0.54 | 1.21 | 1.32 |
| | 2 | 0.15 | 0.08 | 0.48 | 0.57 | 1.03 |
| | 3 | 1.81 | 0.10 | 0.10 | 0.36 | 0.03 |
| | 4 | 1.56 | 4.35 | 2.67 | 0.52 | 2.11 |
| | 5 | 2.65 | 0.27 | 0.11 | 0.78 | 1.65 |
| | 6 | 0.66 | 0.56 | 0.16 | 1.06 | 0.08 |
| | 7 | 2.78 | 0.23 | 0.45 | 0.59 | 0.62 |
| | 8 | 0.72 | 2.08 | 0.90 | 2.90 | 4.40 |
| | 9 | 1.45 | 1.61 | 0.43 | 1.68 | 0.95 |
| | 10 | 2.67 | 2.40 | 0.16 | 1.03 | 0.93 |

Example 6

Determination of Evolution of the Dimensions of Diabetic Foot Ulcers (DFU) Under Treatment The guarantee of proper positioning and reproducibility allowed the quantitative evaluation of the DFU cicatrization kinetics by measuring the DFU area and volume changes during the treatment with EGF. The MRI of 25 DFU patients, taken in identical positions by the system and method of the invention, allowed the measurement of the lesion sizes, with amazing accuracy.

Figure 9A:
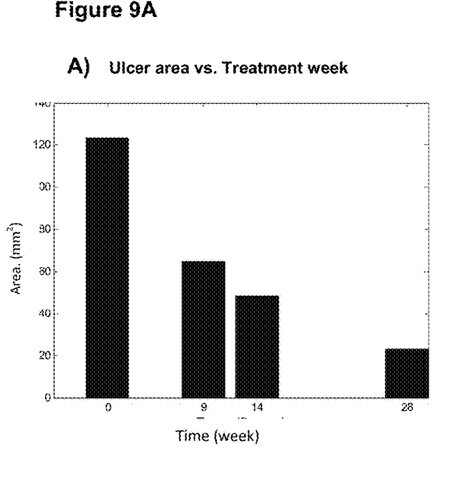
Figure 9B:
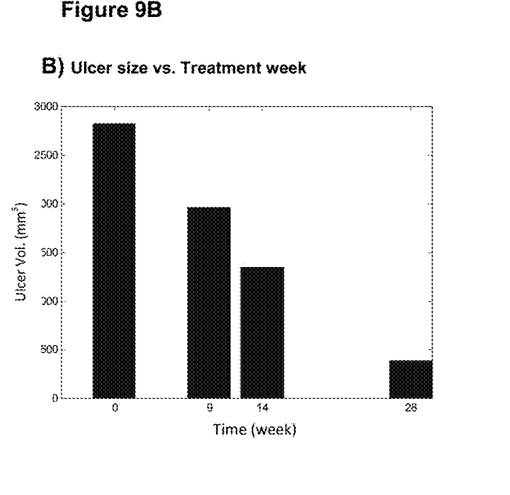

In FIG. 8 appear the axial MRI sections of one of the studied patients. The first MRI was taken before treatment with EGF, the second one was taken at week 9, the third one was taken at week 14 and the fourth one was taken in the 28th week of treatment application. Moreover, in FIG. 9 are the quantitative variations of the areas (FIG. 9A) and volumes (FIG. 9B) of the lesions during the treatment, which demonstrates the response to it. The decrease in the size of the lesion area was 6.5 times, and in the volume was 11.2 times for the referred patient.

Example 7

Figure 10A:
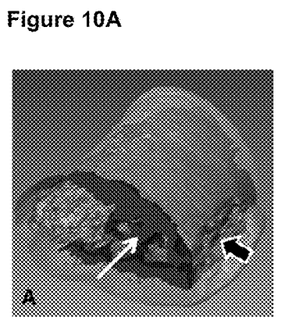
Figure 10B:
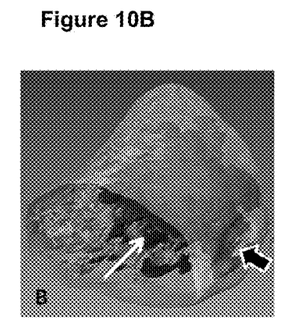
Figure 10C:
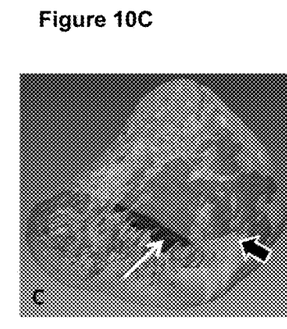

Determination of Evolution of the Edema Volume in the Feet of Patients with Inflammatory Processes The guarantee of the feet correct positioning, and its reproducibility with the system and method of the invention, allowed the quantitative evaluation of the kinetics of edema volume changes (swelling) due to the DFU; which is applicable to any other pathology associated with edema. For the 25 patients evaluated in Example 6, the values of the edema volumes were determined, throughout the treatment period. An example of the behavior of edema in DFU patients, treated with EGF, is shown in FIG. 10. As it can be seen, there is a noticeable decrease in the volume of edema as a result of treatment.

Figure 11:
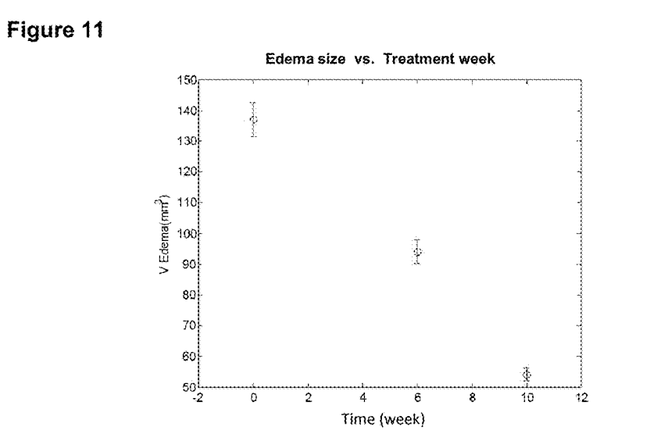
FIG. 11. Variation of the edema volume in a DFU patient. A. Before treatment; B. at week 6; and C. at week 10 of the treatment with EGF.

The rate of change of edema with respect to treatment time can be calculated from the values shown in FIG. 11. At the same is seen that the volume of edema in the patient is 137 $cm^3$ before treatment, while said volume is 54 $cm^3$ at week 10 of treatment.

Example 8

Quantitative Evaluation by MRI of the Texture Evolution of Foot Lesions

A reproducible position of the feet, as a result of the system and method of the invention, allowed recording the Diffusion MRI of patients with DFU, at different times after the beginning of treatment with EGF, and from them the Apparent Diffusion Coefficients (ADC) were calculated in the 25 patients of Example 6. ADC is a complex function of several properties, including the texture of the tissue where the measurement takes place. Only the guarantee of the position accuracy enabled to establish that the relationship of the ADC were a function depending solely on texture changes.

Figure 12:
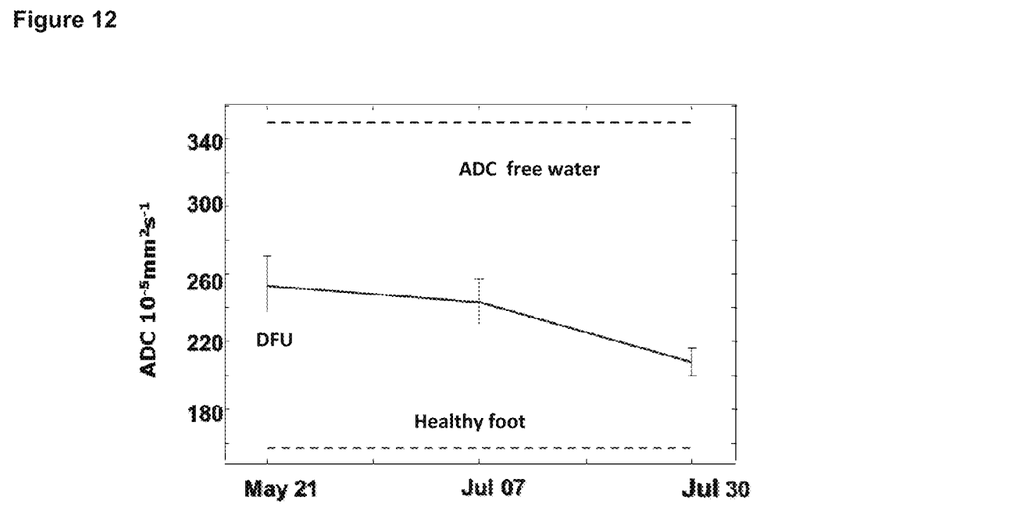
FIG. 12. Apparent Diffusion Coefficient (ADC) measured starting from the MRI in the area of the DFU of the affected foot, compared to the equivalent area in the healthy foot and the free water ADC as a control. For the foot affected with DFU, in the figure is represented the ADC measured during the treatment with EGF.

In FIG. 12 is shown the ADC measured for both feet of a patient with DFU, and the ADC measured for the healthy and the affected foot is compared with the ADC of free water. It is observed that the ADC curve of the foot affected with DFU approaches the values of the healthy foot as the treatment take place.

Figure 13A:
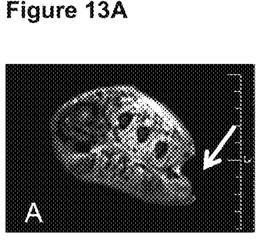
Figure 13B:
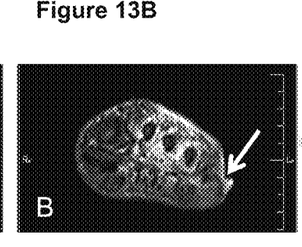
Figure 13C:
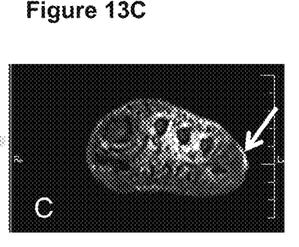

Quantification of changes in the molecular mobility in the lesions and their edges, through MRI, gives unexpectedly valuable information to assess the response to treatment and the onset of the granulation and epithelization processes in the DFU. In FIG. 13 are plotted three MRI (axial sections), wherein the process of wound cicatrization and the emergence of new epithelial tissue are observed. This new tissue is visualized as a hyperintense area marked with an arrow in FIG. 13C. This procedure also allows similar quantitative evaluations of other lesions, such as burns.

Example 9

Quantitative MRI Evaluation of the Evolution of In Vivo Metabolic Activity in Diabetic Foot Ulcers (DFU)

The guarantee of reproducibility of the position of the feet is an essential condition to perform quantitative follow-up studies, of the metabolic activity of foot diseases, from "in vivo" MRS studies whether mono voxel or multi-voxel. The guarantee of the exact location of the voxel is a necessary condition to compare the spectra over serial studies, and assess the response to therapy. Once both feet and lower parts of the legs are placed, it is possible to ensure that the voxels in size, position and orientation are the same through the longitudinal studies. Two lines are highlighted in the spectra, corresponding to the Lipids (Lip) and Creatine (Cr). The MRS amplitudes of healthy foot are at least twofold the ones of the foot affected by DFU. Also, the ratio of amplitudes Lip/Cr changes from the spectrum of the healthy foot to the foot affected by DFU, which is one of the biomarkers of the status of DFU.

Example 10

Evaluation of the Evolution of an Osteomyelitis Patient

Figure 14A:
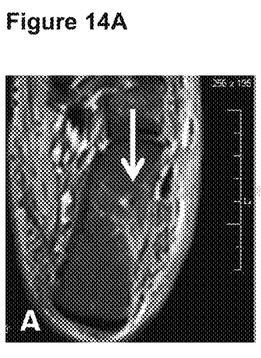
Figure 14B:
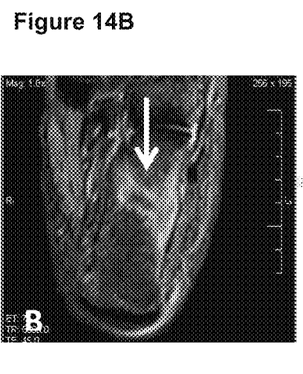
Figure 14C:
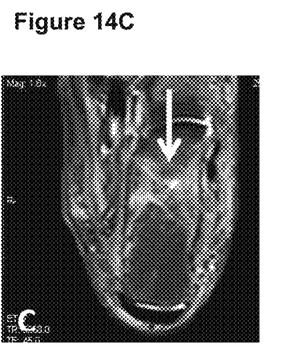

In FIG. 14, the MRI of the calcaneus of a single patient are reflected, taken at three different time points, in the same positioning conditions. The volume of the bone edema was measured from the coronal MRI sections represented in said Figure. The volume of the bone infection, for the referred patient, increased from 8625 mm$^3$ to 27049 mm$^3$.

The invention claimed is:

1. A magnetic resonance imaging (MRI) system to control the orientation of a foot of an individual during a MRI scanning process, the system comprising a foot positioning device, wherein said foot positioning device comprises:
   (a) a foot support section that includes:
      1. a foot support surface to situate said foot of said individual in a fixed position relative to the foot positioning device; wherein said foot support surface comprises at least two image marker elements that are visible when MRI images are recorded;
      2. an arch for a heel adapted to be positioned behind the heel of the individual and sliding regarding said foot support surface;
      3. means to fix the foot of the individual on said foot support surface during the scanning process;
   (b) a leg support section including:
      1. a leg support to situate a leg of said individual in a fixed position regarding the foot positioning device;
      2. means to fix said leg of the individual to said leg support during the scanning process;
   (c) a foot positioning device base adapted to allow that the foot support surface and the leg support section be fixed in said base and positioned on a scanning bed; wherein said foot positioning device is adapted to be inserted into a radiofrequency (RF) coil of the MRI system for scanning in a reproducible position regarding an axis of a static magnetic field of said MRI system.

2. The system according to claim 1, wherein said foot positioning device base is adapted to allow that said foot support section could be placed in a series of fixed positions indicated on a scale regarding said foot positioning device base.

3. The system according to claim 1, wherein the at least two image marker elements are located in parallel to said foot support surface and define a plane of a magnetic resonance image.

4. The system according to claim 1, wherein said foot positioning device comprises material not visible under visualization of magnetic resonance images.

5. The system according to claim 4, wherein said material is polyvinyl chloride.

6. The system according to claim 1, wherein said foot positioning device comprises an additional foot support surface, an additional arch for an additional heel, and an additional leg support, wherein said additional foot support surface, additional arch, and an additional leg support are positioned on the foot positioning device base.

7. A method to control the orientation of a foot of an individual regarding a magnetic resonance imaging system during a magnetic resonance imaging scanning process, the method comprising:
   (a) situating a foot positioning device in a fixed and reproducible position in a radiofrequency coil of the magnetic resonance imaging system;
   (b) locating the foot of the individual in the foot positioning device while the foot positioning device is in said fixed and reproducible position with regard to image marker elements;
   (c) recording first images of magnetic resonance imaging to check correct foot positioning;

(d) optionally correcting the foot positioning regarding the image marker elements and the foot positioning device in the magnetic resonance imaging system; and optionally
(e) recording second magnetic resonance images;
wherein said foot positioning device is a device comprising:
a foot support section that includes a foot support surface to situate said foot of said individual in a fixed position relative to the foot positioning device; wherein said foot support surface comprises said image marker elements, wherein said image marker elements are visible when magnetic resonance imaging images are recorded; an arch for a heel adapted to be positioned behind the heel of the individual and sliding regarding said foot support surface; means to fix the foot of the individual on said foot support surface during the scanning process; a leg support section including a leg support to situate a leg of said individual in a fixed position regarding the foot positioning device; means to fix said leg of the individual to said leg support during the scanning process; a foot positioning device base adapted to allow that the foot support surface and the leg support section be fixed in said base and positioned on a scanning bed; wherein said foot positioning device is adapted to be inserted into a radiofrequency (RF) coil of a magnetic resonance imaging system for scanning in a reproducible position regarding an axis of a static magnetic field of said magnetic resonance imaging system.

* * * * *